United States Patent
Brown et al.

(10) Patent No.: US 11,510,696 B2
(45) Date of Patent: Nov. 29, 2022

(54) GRAFT PREPARATION AND DELIVERY INSTRUMENTS AND METHOD

(71) Applicant: Smith & Nephew, Inc., Memphis, TN (US)

(72) Inventors: Charles H. Brown, Wellesley, MA (US); Michael C. Ferragamo, Foster, RI (US); William R. Davis, Hingham, MA (US); Jeffrey Wyman, Naples, FL (US)

(73) Assignee: SMITH & NEPHEW, INC., Memphis, TN (US)

( * ) Notice: Subject to any disclaimer, the term of this patent is extended or adjusted under 35 U.S.C. 154(b) by 748 days.

(21) Appl. No.: 16/493,331

(22) PCT Filed: Mar. 6, 2018

(86) PCT No.: PCT/US2018/020999
§ 371 (c)(1),
(2) Date: Sep. 12, 2019

(87) PCT Pub. No.: WO2018/169719
PCT Pub. Date: Sep. 20, 2018

(65) Prior Publication Data
US 2021/0137556 A1   May 13, 2021

Related U.S. Application Data

(60) Provisional application No. 62/471,419, filed on Mar. 15, 2017.

(51) Int. Cl.
| A61B 17/34 | (2006.01) |
| A61B 17/00 | (2006.01) |
| A61L 27/22 | (2006.01) |

(52) U.S. Cl.
CPC ............... *A61B 17/3468* (2013.01); *A61B 2017/00969* (2013.01); *A61B 2017/3454* (2013.01); *A61L 27/225* (2013.01)

(58) Field of Classification Search
CPC ...... A61B 17/3468; A61B 2017/00969; A61B 2017/3454; A61L 27/225; A61F 2/95; A61F 2002/9623
See application file for complete search history.

(56) References Cited

U.S. PATENT DOCUMENTS

| 4,784,607 A | 11/1988 | Francois |
| 4,790,819 A | 12/1988 | Li et al. |
| 5,612,187 A | 3/1997  | Brubaker |

(Continued)

OTHER PUBLICATIONS

Chinese Application No. 201880028514.4 The First Office Action & Search Report dated May 7, 2022.

(Continued)

*Primary Examiner* — Ashley L Fishback
(74) *Attorney, Agent, or Firm* — Burns & Levinson, LLP; Joseph M. Maraia

(57) ABSTRACT

Embodiments of the invention include instruments (100, 200, 400, 1100, 1400, 2100, 2400, 3400) and methods useful in delivering graft material (1) to a surgical site. Some embodiments may particularly be directed to forming a graft (1) and accurately and effectively handling and delivering the graft (1) to a surgical site arthroscopically. Graft material (1) may include blood components such as clotted fibrin derived from a patient's or a donor's blood.

18 Claims, 8 Drawing Sheets

(56) References Cited

U.S. PATENT DOCUMENTS

| | | |
|---|---|---|
| 8,679,076 B2 | 3/2014 | Pierce |
| 8,708,944 B2 | 4/2014 | Pierce et al. |
| 2006/0264964 A1 | 11/2006 | Seifert et al. |
| 2011/0092919 A1 | 4/2011 | Pierce |
| 2015/0148901 A1 | 5/2015 | Napolitano |
| 2015/0182558 A1 | 7/2015 | Pierce |

OTHER PUBLICATIONS

European Application 18713463.0-1122 Communication under Rule 161.

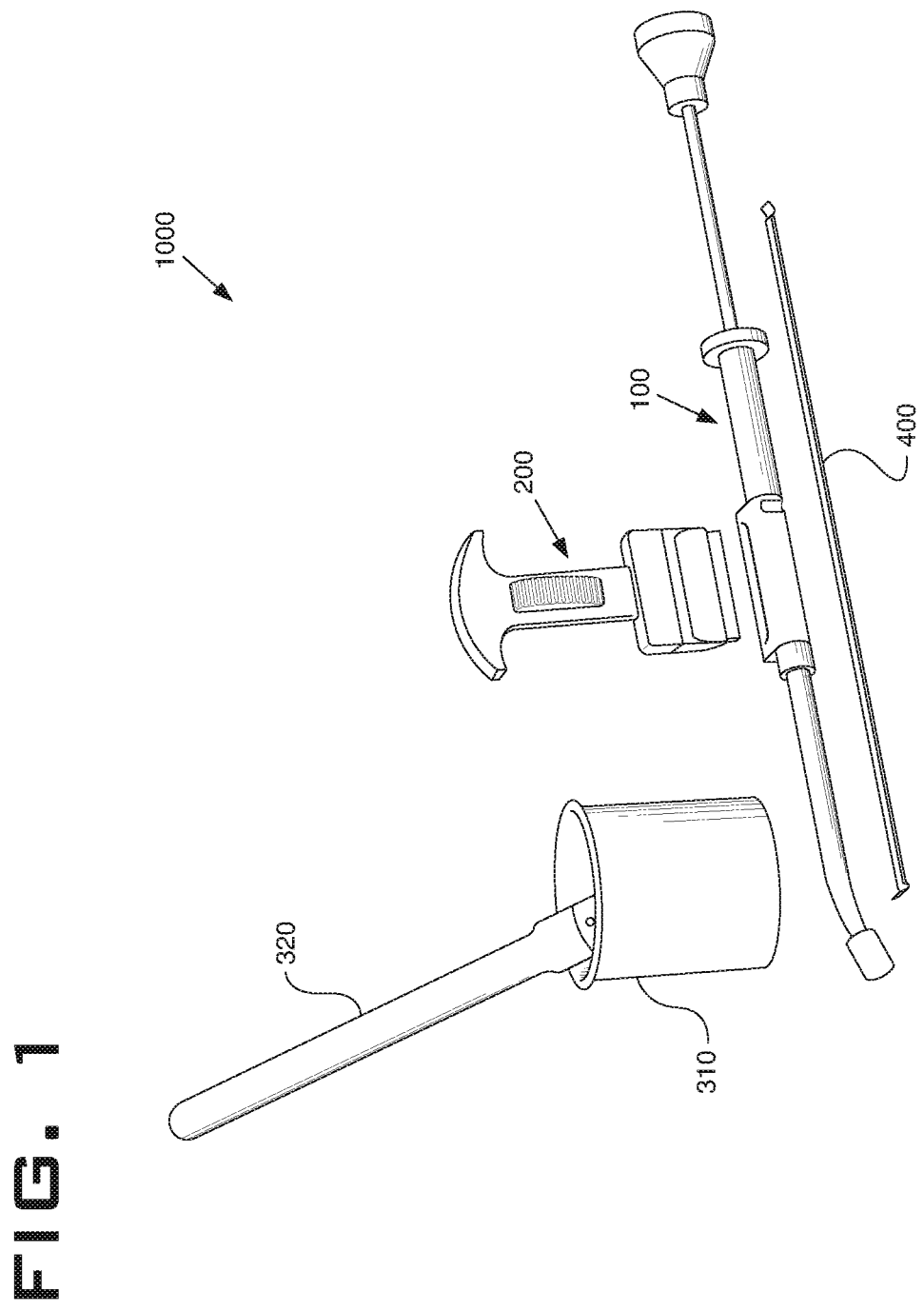

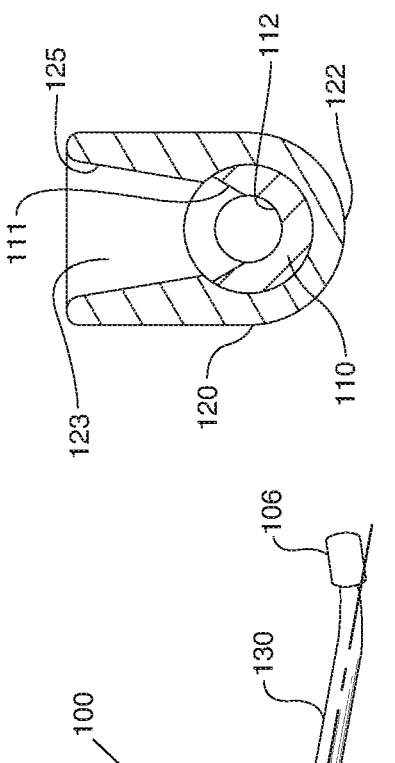
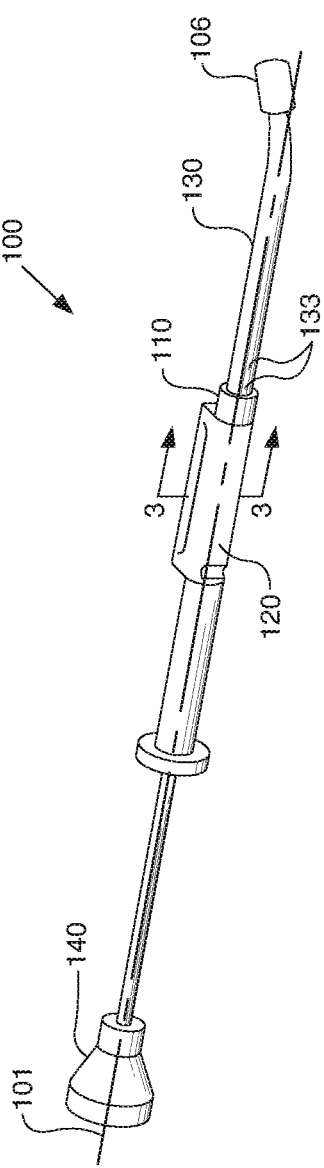
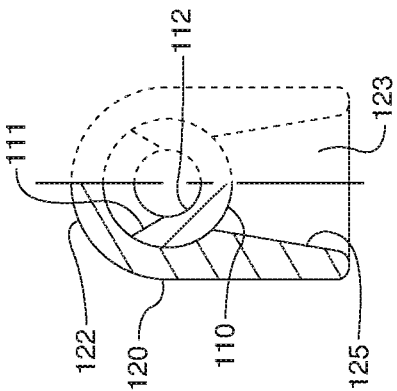
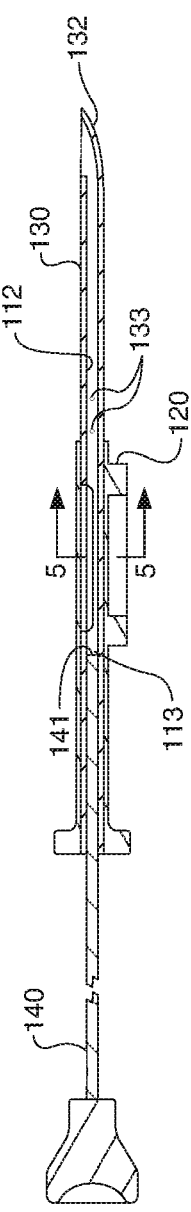

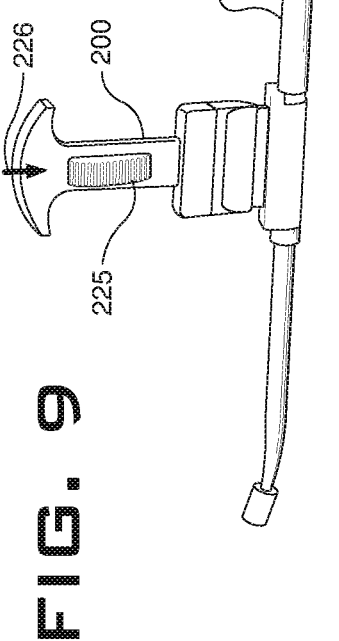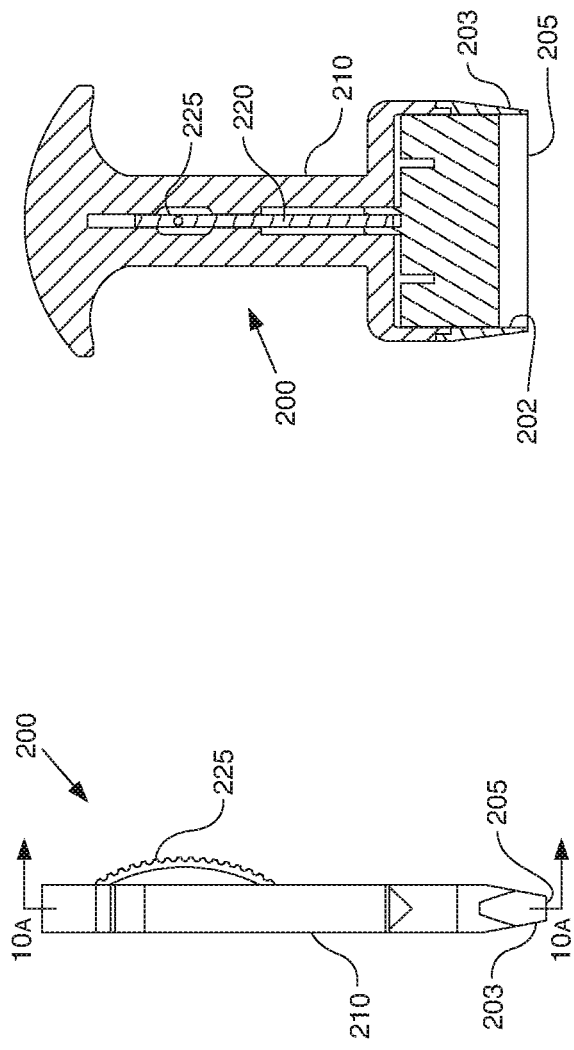

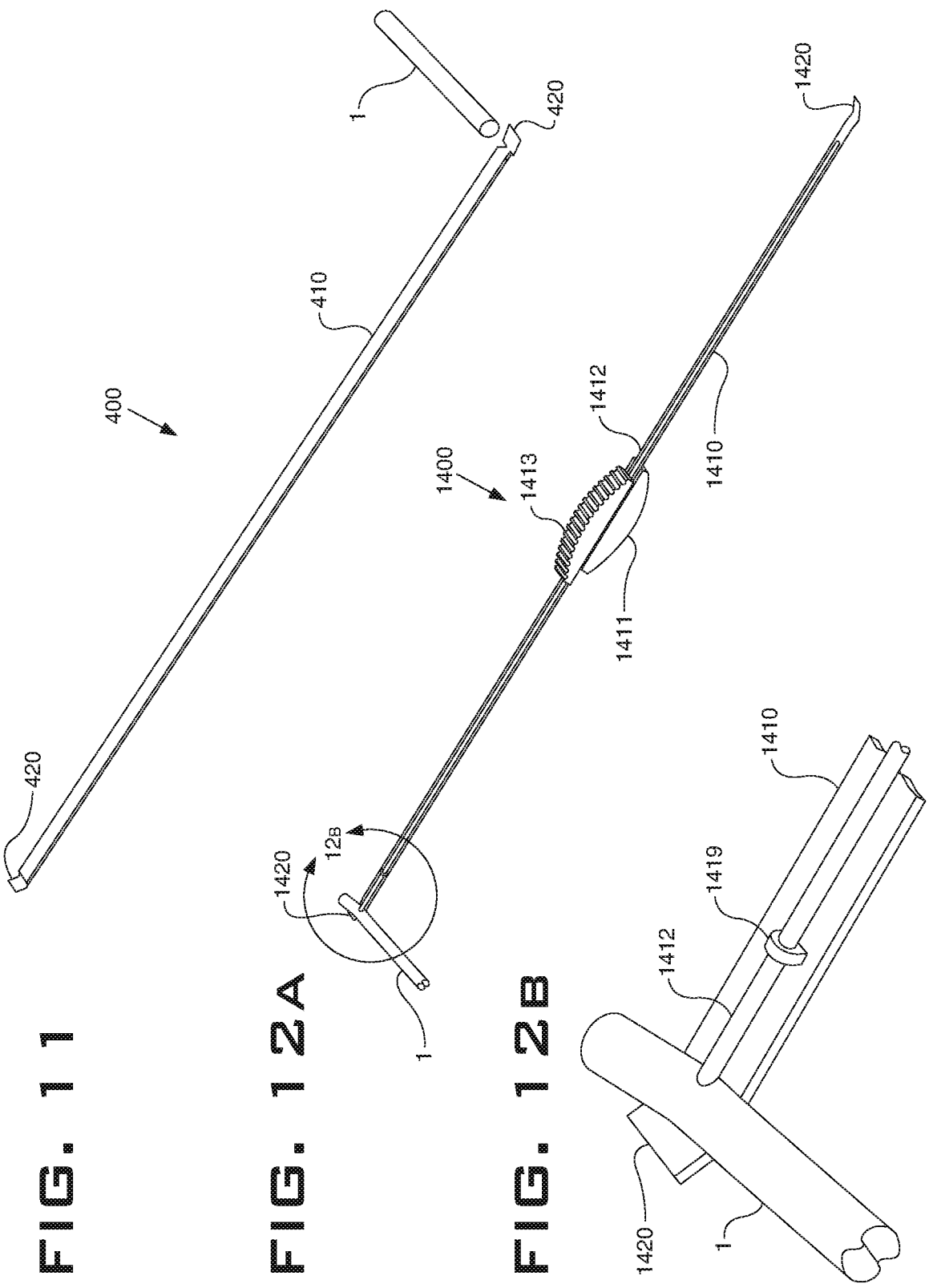

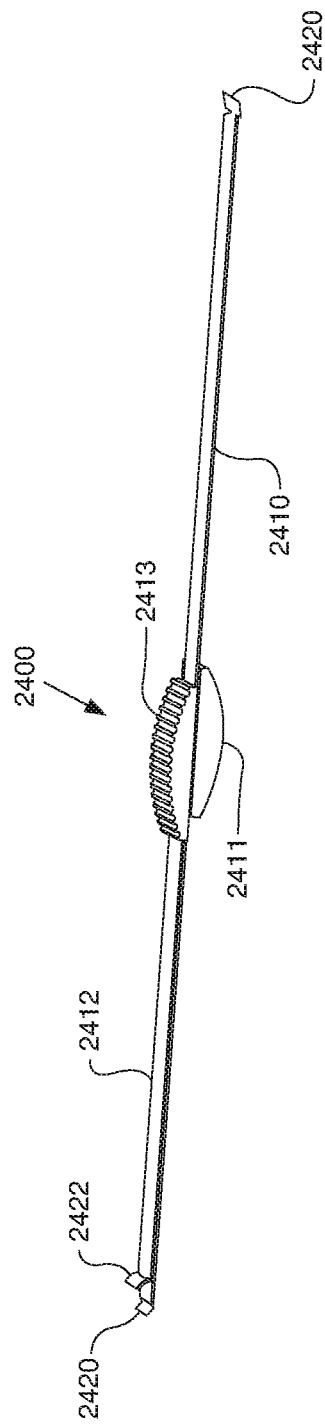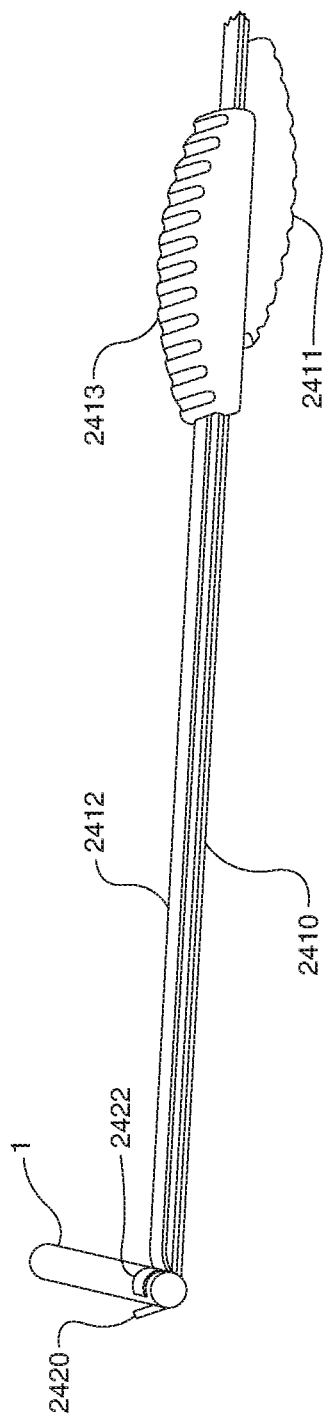

GRAFT PREPARATION AND DELIVERY INSTRUMENTS AND METHOD

CROSS-REFERENCE TO RELATED APPLICATION

This application is the U.S. national phase entry under 35 U.S.C. § 371 of International Application No. PCT/US2018/020999, filed Mar. 6, 2018, entitled "GRAFT PREPARATION AND DELIVERY INSTRUMENTS AND METHOD," which claims priority to and benefit of U.S. Provisional Application No. 62/471,419, filed Mar. 15, 2017, the contents of which are incorporated herein by reference in their entirety for all purposes.

FIELD OF THE INVENTION

The present invention relates generally to the field of medical devices, and more particularly relates to instruments and methods for preparing and delivering tissue healing substances to a tissue repair surgical site. Some embodiments of the invention are specifically directed to preparing and delivering fibrin clots to a tissue repair surgical site.

BACKGROUND

Tissue healing is often enhanced in the presence of concentrations of bioactive substances in blood. For example, meniscal tear healing can be improved in the presence of blood components, especially in concentrated forms. It is believed that meniscal repairs accomplished in conjunction with anterior cruciate ligament reconstruction are particularly advantageous. Insertion of a fibrin clot in a tear prior to the tear being sutured or otherwise closed is advantageous.

It is known in the prior art to draw a patient's blood into a syringe and transfer the blood into a metal pan or a beaker. A glass syringe barrel or a metal rod stirrer may then be used to stir the blood until some coagulation takes place. The time to form a clot depends on materials, sizes, and surface areas of the vessel and stirrer. In some methods, the clot is removed from the stirrer and transferred to a gauze pad. The clot may then be flattened to a consistent thickness and then cut or shaped to make a desired graft shape. Such a clot can be inserted into a damaged tissue site. For meniscal repair, such a clot can be transported arthroscopically through a portal, past a patient's fat pad, and into the meniscal tear. This processes is very technically demanding due to the small size and fragile consistency of the clot in combination with difficulties associated with accessing the tissue repair site.

It would be advantageous to provide instruments and methods that enable more consistent and less technically demanding forming, handling, and delivery of graft material, such as a fibrin clot. For example, it would be an improvement to provide instruments and methods that enabled formation of a graft appropriately dimensioned for efficient and economical insertion of the graft through arthroscopic portals. Some improved embodiments may include additional instruments for handling the graft and delivering the graft to the tissue repair site.

SUMMARY

An embodiment of the invention is an instrument for containing a graft configured for delivery to a surgical site. The instrument may include a hopper with a longitudinal axis along its longest dimension, the hopper being configured to receive graft material through a first opening in the hopper. Some embodiments have a cover with a closed portion and an open portion. The cover may be movably coupled to the hopper such that the first opening is accessible when the cover is in a first position where the open portion aligns with the first opening. The first opening of the embodiment is blocked when the cover is in a second position where the closed portion aligns with the first opening. The instrument may also include a transfer port coupled to the hopper at a second opening in the hopper, wherein the second opening provides a passageway for graft material from the hopper.

Another embodiment of the invention is an instrument set that includes a transfer cutter and an instrument for containing a graft configured for delivery to a surgical site. The transfer cutter may include a body with a cavity that is open through a distal end of the transfer cutter, a cutting tip at the distal end of the transfer cutter, and a graft ejector operable to push a graft collected in the cavity out of the distal end of the transfer cutter. The instrument for containing a graft configured for delivery to a surgical site may include a hopper, a cover, and a transfer port. Embodiments of the hopper include a hopper with a longitudinal axis along its longest dimension configured to receive graft material through a first opening in the hopper. The cover has a closed portion and an open portion. The cover may be movably coupled to the hopper such that the first opening is accessible when the cover is in a first position where the open portion aligns with the first opening and the first opening is configured to dock with the transfer cutter. The instrument may be configured such that the first opening is blocked when the cover is in a second position where the closed portion aligns with the first opening. The transfer port may be coupled to the hopper at a second opening in the hopper, wherein the second opening provides a passageway for graft material from the hopper.

Yet another embodiment of the invention is a method of delivering graft material to a surgical site. The method may include collecting graft material from blood components including blood clotting components and forming the collected graft material into a shape suitable for insertion into a surgical site to promote tissue healing. Method embodiments may also include placing the graft material in a hopper of an instrument for containing the graft material, wherein the graft material is placed through a first opening in the hopper, and closing the first opening in the hopper. After the first opening in the hopper is closed, embodiments may include transferring the graft material out of the hopper through a second opening in the hopper to deliver the graft material to a surgical site.

BRIEF DESCRIPTION OF THE DRAWINGS

FIG. 1 is a perspective view of an embodiment of an instrument set for extracting graft materials from blood and delivering the graft materials to a surgical site.

FIG. 2 is a perspective view of an embodiment of an instrument for containing a graft configured for delivery to a surgical site.

FIG. 3 is a cross-sectional view taken through the instrument illustrated in FIG. 2 with a cover in a first position.

FIG. 4 is a cross-sectional view illustrating how the instrument shown in FIG. 2 appears with the cover in a second position.

FIG. 5 is a cross-sectional view taken through the instrument illustrated in FIG. 4 with the cover in the second position.

FIG. 9 is a perspective view of the instrument for containing a graft configured for delivery to a surgical site shown in FIG. 2 with a transfer cutter docked with the instrument.

FIG. 10 is a side elevation view of the transfer cutter.

FIG. 10A is a cross-sectional view of the transfer cutter shown in FIG. 10.

FIG. 11 is a perspective view of a graft handling instrument of an instrument set embodiment of the invention.

FIG. 12A is a perspective view of a graft handling instrument of an instrument set embodiment of the invention with a segment of graft material captured by the graft handling instrument.

FIG. 12B is a perspective view of a portion of an end of the graft handling instrument of FIG. 12A with a segment of graft material captured by the graft handling instrument.

FIG. 13A is a perspective view of a graft handling instrument of an instrument set embodiment of the invention in a first state of operation.

FIG. 13B is a perspective view of a portion of an end of the graft handling instrument of FIG. 13A in a second state of operation with a segment of graft material captured by the graft handling instrument.

DETAILED DESCRIPTION

Figure 6A:
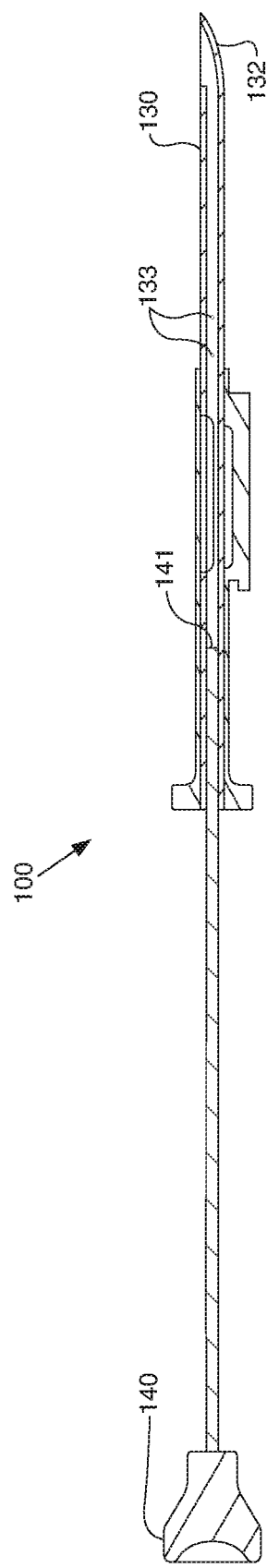
FIG. 6A is the cross-sectional view of FIG. 4 showing a full view of the plunger prior to passage of the plunger through the hopper of the instrument.

An instrument set 1000 is shown in FIG. 1 with an instrument for containing a graft configured for delivery 100, a transfer cutter 200, a cup 310 with a stirrer 320, and a handling instrument 400. The graft referred to herein may be an autograft, an allograft, a synthetic graft, or any substance or composition which is useful in the healing of tissue. For example and without limitation, grafts of various embodiments of the invention may be blood components, such as fibrin derived from blood, collagen, ligaments, tendons, or any combinations or components of any of these.

An embodiment of the instrument for containing a graft configured for delivery 100 is shown in more detail and in operation in FIGS. 2-6B and 9. The illustrated instrument for containing a graft configured for delivery 100 includes a hopper 110 with a longitudinal axis. As shown in FIG. 2, the longitudinal axis of the hopper 110 is coincident with a longitudinal axis 101 of the instrument for containing a graft configured for delivery 100. The hopper 110 depicted is configured to receive graft material through a first opening 111 (FIGS. 3 and 5). The hopper 110 has a generally cylindrical shape extending along its longitudinal axis. In this embodiment, graft material may be compressed into the cylindrical shape of the hopper 110 to form the graft material into a cylindrical shape. In other embodiments, a graft preformed into a cylindrical shape may be inserted into the hopper 110. Graft material of any functional shape may be used in other embodiments and need not necessarily conform to the precise size and shape of the hopper 110. The illustrated first opening 111 in the hopper 110 extends along a longitudinal side of the hopper 110 through which the hopper 110 may be side-loaded with graft material.

The instrument for containing a graft configured for delivery 100 depicted includes a cover 120 movably coupled to the hopper 110 such that there is an unobstructed pathway to an interior of the instrument when the cover 120 is in a first position, such as the position of the cover 120 in FIGS. 2, 3, and 9. The first opening 111 is shown substantially blocked to substantially block the pathway to the interior of the instrument when the cover 120 is in a second position, such as the position of the cover 120 in FIGS. 4-6A. Considered under another nomenclature, the cover 120 has a closed portion 122 and an open portion 123, as shown in FIGS. 3 and 5. The cover 120 is movably coupled to the hopper 110 such that the first opening 111 is accessible when the cover 120 is in first position (FIGS. 2, 3, and 9) where the open portion 123 aligns with the first opening 111 and the first opening 111 is configured to dock with the transfer cutter 200. The first opening 111 is blocked when the cover 120 is in the second position (FIGS. 4-6A) where the closed portion 122 aligns with the first opening 111 in the hopper 110. In the illustrated embodiment, the cover 120 is rotatable about the longitudinal axis of the hopper 110 between the first position (FIGS. 2, 3, and 9) and the second position (FIGS. 4-6A).

Figure 7:
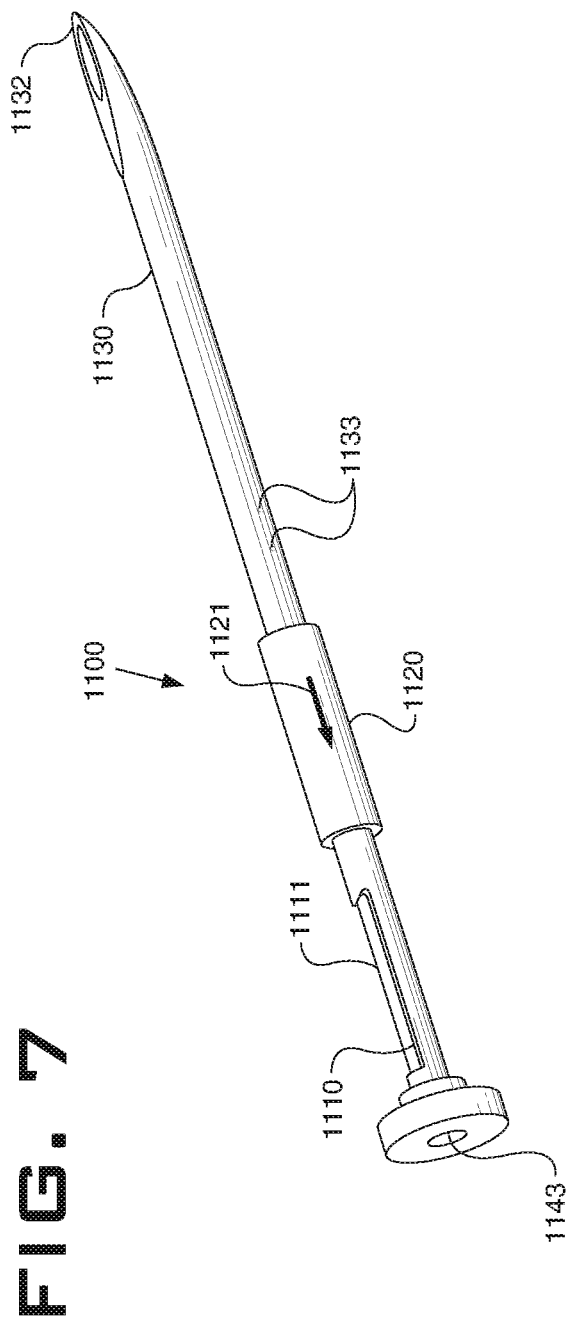
FIG. 7 is a perspective view of a first alternative embodiment of an instrument for containing a graft configured for delivery to a surgical site.
Figure 8:
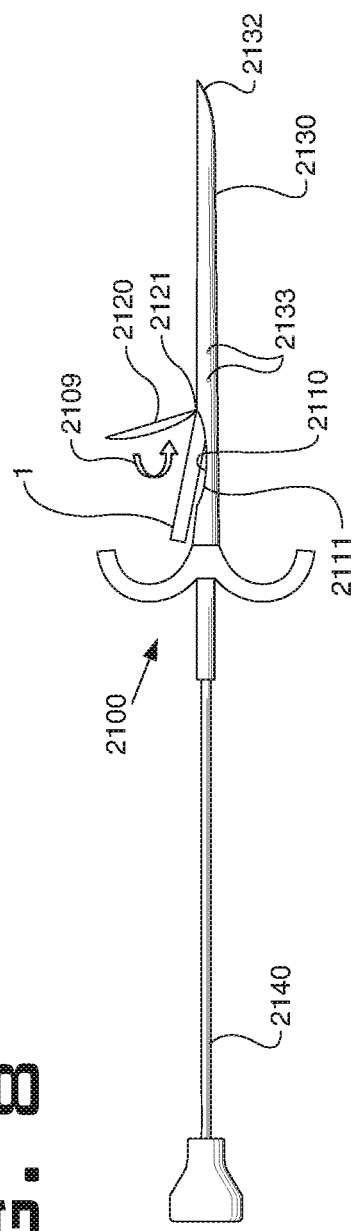
FIG. 8 is a perspective view of a second alternative embodiment of an instrument for containing a graft configured for delivery to a surgical site.

In other embodiments, the movement of a cover relative to a hopper to selectively obstruct a pathway to the interior of the instrument may be any other functional movement. For example, in FIG. 7, an instrument for containing a graft configured for delivery 1100 includes a hopper 1110 that may be selectively blocked by a cover 1120 by movement along a longitudinal axis of the instrument, as indicated by an arrow 1121. A first open position of the cover 1120 is illustrated in FIG. 7. The cover 1120 may be close to facilitate further motion of the graft through the instrument for containing graft configured for delivery 1100. In another example in FIG. 8, and instrument for containing a graft configured for delivery 2100 includes a hopper 2110 that may be selectively blocked by a cover 2120 that rotates about a hinge 2121 with an axis that is transverse to the longitudinal axis of the instrument. As indicated by motion arrow 2109, a graft 1 may be inserted into the hopper 2110 when the cover 2120 is in a first open position, as illustrated in FIG. 8. The cover 2120 may be closed to facilitate further motion of the graft through the instrument for containing graft configured for delivery 2100.

As most easily seen in FIGS. 3 and 5, the cover 120 includes a bin 125. The bin 125 is a portion of the cover 120 adjacent to the open portion 123 of the cover 120. The bin 125 is positioned over the first opening 111 in the hopper 110 when the cover 120 is in the first position, as illustrated in FIGS. 2, 3, and 9. The bin 125 of the illustrated embodiment is particularly configured to receive or dock with the distal end 203 of the transfer cutter 200, as shown in FIG. 9, to enable efficient transfer of a graft from the transfer cutter 200 to the hopper 110 by activation of the slider button assembly 225 in the direction of arrow 226. Any other effective mechanism for docking between the instrument for containing a graft configured for delivery 100 and the transfer cutter 200 may be used in other embodiments of the invention.

A transferred port embodied to include a tube 130 is coupled to the hopper 110 at a second opening 112 in the hopper 110 in the illustrated embodiment. The tube 130 shown extends away from the hopper 110. Graft material may be passed out of the hopper 110 through the second opening 112 and into the tube 130. Therefore, the second opening 112 provides a passageway for graft material from the hopper 110. In some embodiments, such as the illustrated embodiment the first opening 111 and the second opening 112 are separate openings, which in some cases provides advantages. However, in other embodiments, a first opening and a second opening may have shared elements.

Figure 6B:
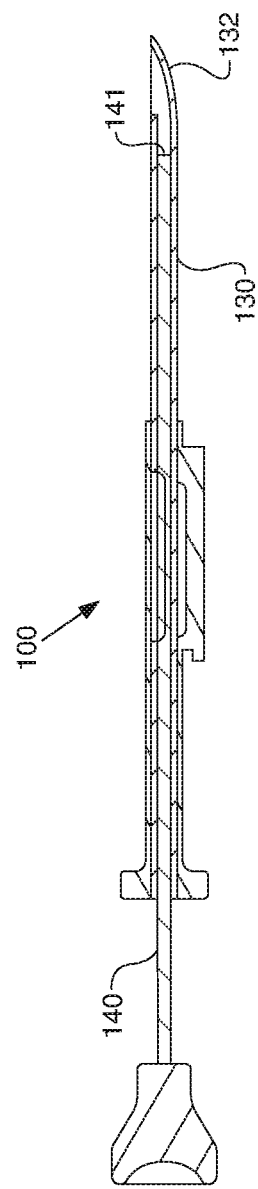
FIG. 6B is the cross-sectional view of FIG. 4 shown following passage of a plunger through the hopper of the instrument.

The tube 130 includes a distal end with a beveled tip 132 configured to be inserted into a tissue defect at the surgical site. The beveled tip 132 illustrated in FIGS. 4, 6A, and 6B is a single planar bevel cut along an acute angle to the longitudinal axis of the instrument for containing a graft configured for delivery 100. In other embodiments, a beveled tip may include curved cuts, multiple planar cuts, multiple curved cuts, or any combination of cuts or shaping that result in a tapered profile. The beveled tip 132 is configured for passage of the graft material through a bore that intersects the bevel cut. Similarly, the instruments illustrated in FIGS. 7 and 8 include a beveled tip 1132, 2132. A protective cover 106 is shown in FIG. 2 capping the beveled tip 132 to guard against inadvertent tissue damage or operator injury prior to use of the instrument. The tube 130 also includes weep holes 133 (FIGS. 2, 4, and 6A) through which pressure may be relieved as graft material is passed through the tube 130. In particular, as a graft is moved through the tube 130, the graft may form a complete or partial seal with an inner wall of the tube 130. This may increase the amount of force necessary to move the graft through the tube 130. The weep holes 133 allow for some of the pressure created behind the complete or partial seal to exit out of the tube 130 at the weep holes and thereby reduce the pressure within the tube 130. Similarly, the instruments illustrated in FIGS. 7 and 8 include weep holes 1133, 2133.

The instrument for containing a graft configured for delivery 100 also may include a plunger 140 configured to pass through a third opening 113 (FIG. 4) in the hopper 110 on the opposite side of the hopper 110 from the second opening 112. The plunger 140 includes a distal end 141 (FIGS. 4, 6A, and 6B). As illustrated in the progression between FIGS. 6A and 6B, at least the distal end 141 of the plunger 140 is designed to be at least in part advanced through the third opening 113, the hopper 110, and the second opening 112 to push contents of the hopper 110 out of the second opening 112. Although a pushing plunger 140 is described in the illustrated embodiment, any structure that pushes, pulls, or otherwise moves a graft through the instrument may be a plunger in other embodiments of the invention. Similarly, a hole 1143 for a plunger and a plunger 2140 are illustrated respectively in FIGS. 7 and 8.

The instrument set 1000 illustrated in FIG. 1 includes the instrument for containing a graft configured for delivery to a surgical site 100 in combination with a transfer cutter 200 (FIGS. 1 and 9-10A). The illustrated transfer cutter 200 includes a body 210 with a cavity 202 that is open through a distal end 203 of the transfer cutter 200 and a cutting tip 205 at the distal end 203 of the transfer cutter 200. The cavity 202 of the illustrated embodiment has a generally cylindrical shape. However, in other embodiments, a cavity may be angular, such as a rectangular or square cubical shape, or any other intermediary or final functional shape to which a graft may be formed or collected and effectively used in a surgical procedure. The cutting tip 205 is in the configuration of a box chisel with four substantially straight cutting blades that form a generally rectangular shape with one another. Any other effective shape of cutting tip or cutting blades may be used, and all cutting blades would not necessarily have to extend along the entire perimeter of the cutting tip. The transfer cutter 200 embodiment shown also includes a graft ejector 220 operable to push a graft collected in the cavity 202 out of the cutting tip 205 of the transfer cutter 200. The graft ejector 220 depicted includes a slider button assembly 225 that may be advanced by a user in the direction of arrow 226 (FIG. 9) to move the graft ejector 220 relative to the body 210 and eject a graft collected in the cavity 202 out of the transfer cutter 200. Any other effective mechanism for ejecting a graft from a transfer cutter may be used in other embodiments.

The illustrated instrument set 1000 includes the cup 310 with the stirrer 320. The cup 310 may be made from any type of material able to be sterilized effectively that will not unnecessarily adhere to the graft material being prepared. For example and without limitation, the may be made from glass or stainless steel. Embodiments of the cup are not limited to a cylindrical container open at one end and may be any shape or size of effective container. The stirrer 320 is designed to have a surface on or near its distal end to which graft material, such as fibrin material, will form when the stirrer 320 is used to agitate, for example, blood that is contained within the cup 310. For example and without limitation, the stirrer 320 in whole or in part may be made from glass or stainless steel. The portion of the stirrer 320 to which fibrin material is designed to adhere may include a roughened surface, a scored surface, an etched surface, or the like.

The illustrated instrument set 1000 includes the handling instrument 400 and other instrument set embodiments may include any other effective handling instrument. For example and without limitation, handling instruments 1400, 2400, 3400 illustrated in FIGS. 12A-14C may be used as part of an instrument set. The handling instrument 400 includes a shaft 410 and paddles 420 that are coupled to the shaft 410 at opposite longitudinal ends of the handling instrument 400. The illustrated paddles 420 are generally flat and have a slight lengthways curvature to better enable coupling with and manipulating a graft such as the generally cylindrical graft 1. Some embodiments of the handling instrument 400 may include paddles with different curvatures or shapes at respective ends to enable various angles of approach to a graft to be handled or for the handling of different types of graft. Other embodiments of the handling instrument would not necessarily include a paddle or other handling component on each end of the handling instrument.

The handling instrument 1400 illustrated in FIGS. 12A and 12B includes a shaft 1410, an actuator 1412 that is slidable relative to the shaft 1410, and paddles 1420 that are coupled to the shaft 1410 at opposite longitudinal ends of the handling instrument 1400. The shaft 1410 includes a grip 1411, and the actuator 1412 also includes a grip 1413. The grips 1411, 1413 may be moved relative to one another along a longitudinal axis of the handling instrument 1400 to move the actuator 1412 relative to the shaft 1410. The illustrated handling instrument 1400 includes a bracket 1419 coupled to the shaft 1410 with an opening through which the actuator 1412 is able to slide. As shown in FIG. 12B, the actuator 1412 has been moved relative to the shaft 1410 to grasp the graft 1, in this case by slightly puncturing the graft 1, between the actuator 1412 and one of the paddles 1420. The illustrated paddles 1420 are generally flat and have a slight lengthways curvature to better enable coupling with and manipulating a graft such as the generally cylindrical graft 1. The illustrated handling instrument 1400 includes a substantially similar end at the opposite end of the instrument. Some embodiments of the handling instrument 1400 may include paddles with different curvatures or shapes at respective ends to enable various angles of approach to a graft to be handled or for the handling of different types of graft. Other embodiments of the handling instrument would not necessarily include a paddle or other handling component on each end of the handling instrument.

The handling instrument 2400 illustrated in FIGS. 13A and 13B includes a shaft 2410, an actuator 2412 that is slidable relative to the shaft 2410, and paddles 2420 that are coupled to the shaft 2410 at opposite longitudinal ends of the handling instrument 2400. The shaft 2410 includes a grip 2411, and the actuator 2412 also includes a grip 2413. The grips 2411, 2413 may be moved relative to one another along a longitudinal axis of the handling instrument 2400 to move the actuator 2412 relative to the shaft 2410. As illustrated, the actuator 2412 has been moved relative to the shaft 2410 to grasp the graft 1 between a raised end 2422 of the actuator 2412 and one of the paddles 2420. The illustrated paddles 2420 are generally flat and have a lengthways curvature to better enable coupling with and manipulating a graft such as the generally cylindrical graft 1. The illustrated handling instrument 2400 includes only a paddle 2420 at the end opposite from the end illustrated in FIG. 13B. Some embodiments of the handling instrument 2400 may include paddles with different curvatures or shapes at respective ends to enable various angles of approach to a graft to be handled or for the handling of different types of graft. Other embodiments of the handling instrument would not necessarily include a paddle or other handling component on each end of the handling instrument.

Figure 14A:
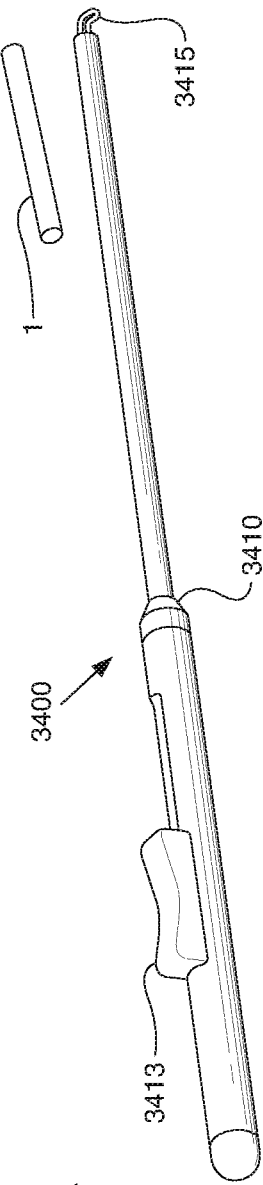
FIG. 14A is a perspective view of a graft handling instrument of an instrument set embodiment of the invention in a first state of operation and shown with a segment of graft material.
Figure 14B:
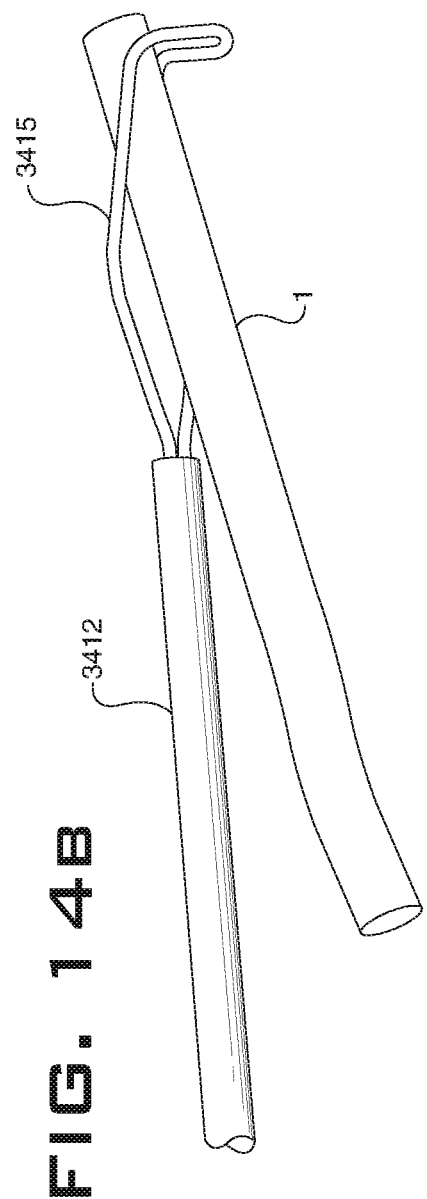
FIG. 14B is a perspective view of a portion of an end of the graft handling instrument of FIG. 14A in a second state of operation with a segment of graft material captured by the graft handling instrument.
Figure 14C:
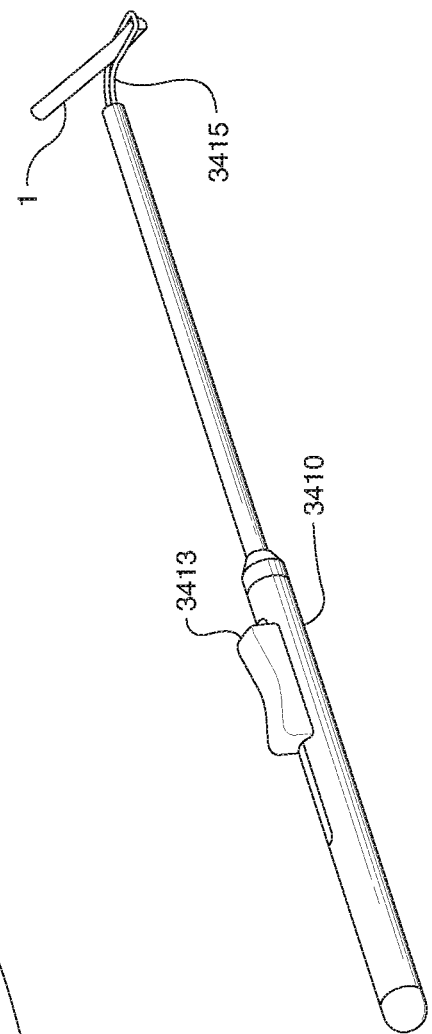
FIG. 14C is a perspective view the graft handling instrument of FIG. 14A in a third state of operation with a segment of graft material being manipulated with the graft handling instrument.

The handling instrument 3400 illustrated in FIGS. 14A-14C includes a shaft 3410, an actuator 3412 that is slidable relative to the shaft 3410, and a grasper 3415 coupled to the actuator 3412. The actuator 3412 also includes a grip 3413. The grip 3413 may be moved relative to the shaft 3410 along a longitudinal axis of the handling instrument 3400 to move the actuator 3412 relative to the shaft 3410. The grasper 3415 includes a bent wire that when moved out of a distal end of the shaft 3410 is biased to spring open wide enough to surround a graft 1, as illustrated in FIG. 14B. The distal end of the bent wire of the grasper 3415 is hooked so that a graft may be manipulated with the hook, as shown in FIG. 14C. The illustrated handling instrument 3400 includes only one functional end, but other embodiments may include a paddle or other graft handling device at the opposite end of the instrument.

An embodiment of the invention is a method of delivering graft material to a surgical site. The surgical site may be any surgical repair site that may benefit from the delivery of a graft material. For example and without limitation, the surgical site may be a meniscal repair site within a patient's knee such as a tear that is to be sutured or otherwise closed or amended. Acts of the method embodiment may include collecting graft material from blood components, including blood clotting components, and forming the collected graft material into a shape suitable for insertion into a surgical site to promote tissue healing. Specifically, a patient's or a donor's blood may be collected in the cup 310 illustrated in FIG. 1, and the stirrer 320 may be used to stir or agitate the blood to promote clotting on a surface of the stirrer 320. Fibrin sheets from the clots that deposit on the stirrer 320 may then be unwrapped from the stirrer 320 and deposited in a single layer or in multiple layers on a surface. These deposits may then be further formed into a shape suitable for insertion into a surgical site. For example, the cutting tip 205 of the transfer cutter 200 described herein may be pressed onto the single or multiple layers of graft material to cut segments of the graft material in the perimeter shape of the cutting tip 205. Repeated cutting in this manner will push a larger mass of graft material further into the cavity 202 of the transfer cutter 200. The graft that is pressed into the cavity 202 will be conformed to the shape of the cavity 202 if pressed far enough into the cavity 202. An additional tool or instrument may be deployed within the perimeter of the cutting tip 205 to further compress and shape the graft to a desired shape and density.

The method may also include placing the graft material in a hopper of an instrument for containing the graft material, such as the hopper 110, through a first opening 111 in the hopper 110. For the instruments illustrated in FIGS. 9-10A, the act of placing the graft material in the hopper 110 includes ejecting the graft material from the cavity 202 of the transfer cutter by pushing the slider button assembly 225 distally to move the graft ejector 220 distally and push the graft out of the transfer cutter 200 and into the hopper 110 while the transfer cutter 200 is in the position depicted in FIG. 9. A similar graft placement could be accomplished with the instruments for containing a graft configured for delivery 1100, 2100, or with any other similar instrument in other embodiments.

Another act of some method embodiments includes closing the first opening in the hopper. For the instruments shown, the first opening 111 in the hopper 110 is closed by rotating the cover 120 from the first position shown in FIGS. 2 and 3 to the second position shown in FIGS. 4 and 5; the first opening 1111 in the hopper 1110 is closed by sliding the cover 1120 from the first position shown in FIG. 7 to a second position in the direction of the arrow 1121; and the first opening 2111 in the hopper 2110 is closed by rotating the cover 2120 from the first position shown in FIG. 8 about a hinge 2121 with an axis that is transverse to the longitudinal axis of the instrument to a second position where the cover 2120 contacts the first opening 2111.

After the first opening in the hopper is closed, method embodiments may include transferring the graft material out of the hopper through a second opening in the hopper to deliver the graft material to a surgical site. For example, after the first opening 111 in the hopper 110 is closed, graft material may be transferred out of the hopper 110 through the second opening 112 (FIGS. 4 and 5) to deliver the graft material to a surgical site. More particularly, graft material of the embodiment depicted is moved through a transfer port, as embodied in the tube 130, and the beveled tip 132 to deliver the graft material to a surgical site. In the case of the instrument of FIG. 7, after the first opening 1111 in the hopper 1110 is closed, graft material may be transferred out of the hopper 1110 through a second opening (not shown) coupled with a tube 1130 transfer port and through the beveled tip 1132. In the case of the instrument of FIG. 8, after the first opening 2111 in the hopper 2110 is closed, graft material may be transferred out of the hopper 2110 through a second opening (not shown) coupled with a tube 2130 transfer port and through the beveled tip 2132.

In the embodiment illustrated in FIGS. 1-6B, the act of transferring the graft material out of the hopper 110 through a second opening 112 in the hopper includes pushing the graft material with a plunger 140 through the hopper 110, the second opening 112, and a third opening 113 in the hopper on the opposite side of the hopper 110 from the second opening 112. Advancement of the plunger 140 is specifically shown in the progression between FIGS. 6A and 6B where a distal end 141 of the plunger 140 is shown passing through (FIG. 6B) the third opening 113 and the second opening 112 of the hopper 110 toward a distal end of the tube 130 with the beveled tip 132. Similarly, the instrument of FIG. 7 includes a hole 1143 through which a plunger may be passed to advance graft out of the hopper 1110 and along and out of the tube 1130. And, the instrument of FIG. 8 illustrates a plunger 2140 that may be passed through the hopper 2110 to advance graft out of the hopper 2110 and along and out of the tube 2130.

Various embodiments of an instrument or instrument set wholly or its components individually may be made from any biocompatible material. For example and without limitation, biocompatible materials may include in whole or in part: non-reinforced polymers, reinforced polymers, metals, ceramics, glass, adhesives, reinforced adhesives, and combinations of these materials. Reinforcing of polymers may be accomplished with carbon, metal, or glass or any other effective material. Examples of biocompatible polymer materials include polyamide base resins, polyethylene, Ultra High Molecular Weight (UHMW) polyethylene, low density polyethylene, polymethylmethacrylate (PMMA), polyetheretherketone (PEEK), polyetherketoneketone (PEKK), a polymeric hydroxyethylmethacrylate (PHEMA), and polyurethane, any of which may be reinforced. Example biocompatible metals include stainless steel and other steel alloys, cobalt chrome alloys, zirconium, oxidized zirconium, tantalum, titanium, titanium alloys, titanium-nickel alloys such as Nitinol and other superelastic or shape-memory metal alloys.

Terms such as distal, away, near, over, and the like have been used relatively herein. However, such terms are not limited to specific coordinate orientations, distances, or sizes, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. An instrument for containing a graft configured for delivery to a surgical site comprising:
   a hopper with a longitudinal axis, the hopper being configured to receive graft material through a first opening in the hopper;
   a cover movably coupled to the hopper such that there is an unobstructed pathway to an interior of the instrument when the cover is in a first position, and the first opening is substantially blocked to substantially block the pathway to the interior of the instrument when the cover is in a second position; and
   a transfer port coupled to the hopper at a second opening in the hopper, wherein the second opening provides a passageway for graft material from the hopper;
   wherein the cover is rotatable about the longitudinal axis of the hopper between the first position and the second position.

2. The instrument of claim 1 wherein the hopper has a generally cylindrical shape extending along its longitudinal axis.

3. The instrument of claim 1 wherein the first opening in the hopper extends along a longitudinal side of the hopper through which the hopper may be side-loaded.

4. The instrument of claim 1 wherein the cover includes a bin that is positioned over the first opening in the hopper when the cover is in the first position.

5. The instrument of claim 1 wherein the transfer port includes a tube that extends away from the hopper through which graft material may be passed out of the hopper.

6. The instrument of claim 5 wherein the tube includes a distal end with a beveled tip configured to be inserted into a tissue defect at the surgical site and configured for passage of the graft material.

7. The instrument of claim 5 wherein the tube includes one or more weep holes through which pressure may be relieved as graft material is passed through the tube.

8. The instrument of claim 1, further comprising a plunger configured to pass through a third opening in the hopper on the opposite side of the hopper from the second opening and be advanced through the third opening, the hopper, and the second opening to push contents of the hopper out of the second opening.

9. An instrument set comprising:
   a transfer cutter comprising:
      a body with a cavity that is open through a distal end of the transfer cutter,
      a cutting tip at the distal end of the transfer cutter, and
      a graft ejector operable to push a graft collected in the cavity out of the cutting tip of the transfer cutter; and
   an instrument for containing a graft configured for delivery to a surgical site comprising:
      a hopper with a longitudinal axis, the hopper being configured to receive graft material through a first opening in the hopper,
      a cover with a closed portion and an open portion, the cover movably coupled to the hopper such that the first opening is accessible when the cover is in a first position where the open portion aligns with the first opening and the first opening is configured to dock with the transfer cutter, and the first opening is blocked when the cover is in a second position where the closed portion aligns with the first opening, and
      a transfer port coupled to the hopper at a second opening in the hopper, wherein the second opening provides a passageway for graft material from the hopper.

10. The instrument set of claim 9 wherein the cavity in the body of the transfer cutter includes a generally cylindrical shape.

11. The instrument set of claim 9 wherein the cutting tip of the transfer cutter is in the configuration of a box chisel.

12. The instrument set of claim 9 wherein the transfer cutter is configured to engage with a bin over the first opening in the hopper when the cover is in the first position to deliver graft into the bin.

13. The instrument set of claim 9, further comprising a plunger configured to pass through a third opening in the hopper on the opposite side of the hopper from the second opening and be advanced through the third opening, the hopper, and the second opening to push contents of the hopper out of the second opening.

14. The instrument set of claim 9, further comprising one or more graft handling instruments configured to manipulate graft material formed in the transfer cutter.

15. A method of delivering graft material to a surgical site comprising:
- collecting graft material from blood components including blood clotting components;
- forming the collected graft material into a shape suitable for insertion into a surgical site to promote tissue healing;
- placing the graft material in a hopper of an instrument for containing the graft material, wherein the graft material is placed through a first opening in the hopper;
- closing the first opening in the hopper; and
- after the first opening in the hopper is closed, transferring the graft material out of the hopper through a second opening in the hopper to deliver the graft material to a surgical site.

16. The method of claim 15 wherein the act of closing the first opening in the hopper includes moving a cover with a closed portion and an open portion from a first position where the open portion of the cover aligns with the first opening in the hopper to a second position where the closed portion of the cover aligns with the first opening in the hopper.

17. The method of claim 16 wherein the act of closing the first opening in the hopper includes moving the cover in a substantially rotary direction relative to the hopper.

18. The method of claim 16 wherein the act of closing the first opening in the hopper includes moving a cover along a longitudinal axis of the hopper to cover the first opening in the hopper.

* * * * *